United States Patent [19]

Wagner

[11] 4,035,848
[45] July 19, 1977

[54] HIP CAPITULUM CAP FOR A HIP JOINT PROSTHESIS

[76] Inventor: Heinz Wagner, P.O. Box 22, Altdorf near Nurnberg, Germany, 8503

[21] Appl. No.: 668,962

[22] Filed: Mar. 22, 1976

[30] Foreign Application Priority Data

Mar. 21, 1975 Germany .............................. 2512407

[51] Int. Cl.² ................................................ A61F 1/24
[52] U.S. Cl. .................................. 3/1.913; 128/92 C; 128/92 CA
[58] Field of Search ................................ 3/1.9–1.913; 128/92 C, 92 CA

[56] References Cited

U.S. PATENT DOCUMENTS 3,521,302   7/1970   Muller ..................................... 3/1.91
3,924,275  12/1975   Heimke et al. ........................ 3/1.912
3,925,824  12/1975   Freeman et al. ...................... 3/1.912

FOREIGN PATENT DOCUMENTS 764,600  12/1956  United Kingdom ........... 128/92 CA
720,092  12/1954  United Kingdom ........... 128/92 CA

*Primary Examiner*—Ronald L. Frinks
*Attorney, Agent, or Firm*—Wigman & Cohen

[57] ABSTRACT

A hip capitulum cap for a hip joint prosthesis is disclosed wherein the cap is shaped substantially in the form of half a hollow sphere. The inner spherical surface of the sphere is provided with an uneven contact surface comprising one or more ribs. An opening is disposed through the cap preferably at the vertex thereof and is smoothly enlarged at its intersection with the inner and outer surfaces of the cap.

5 Claims, 3 Drawing Figures

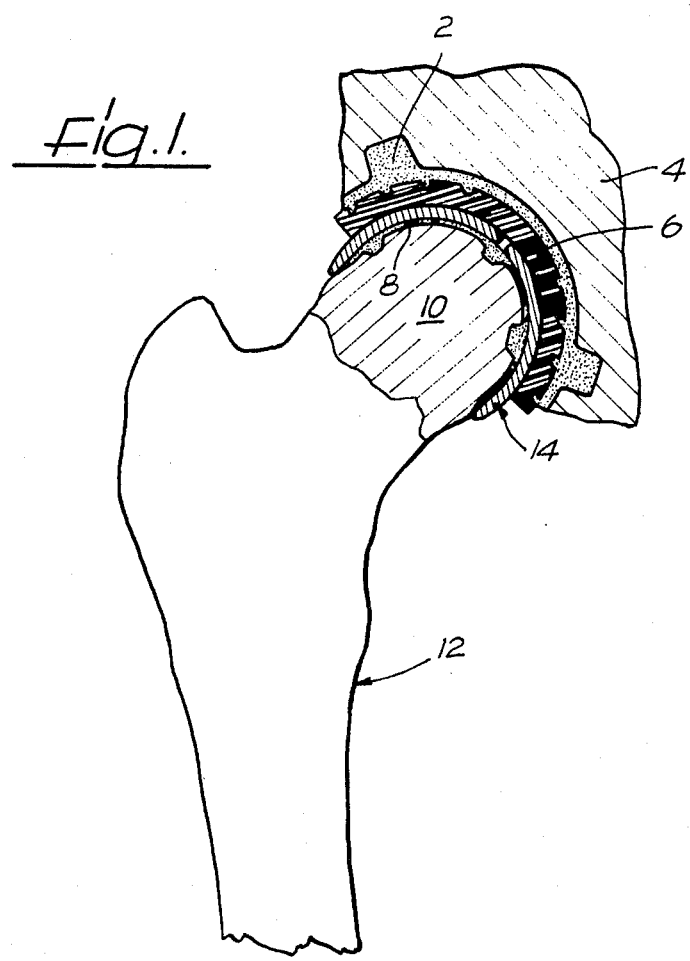

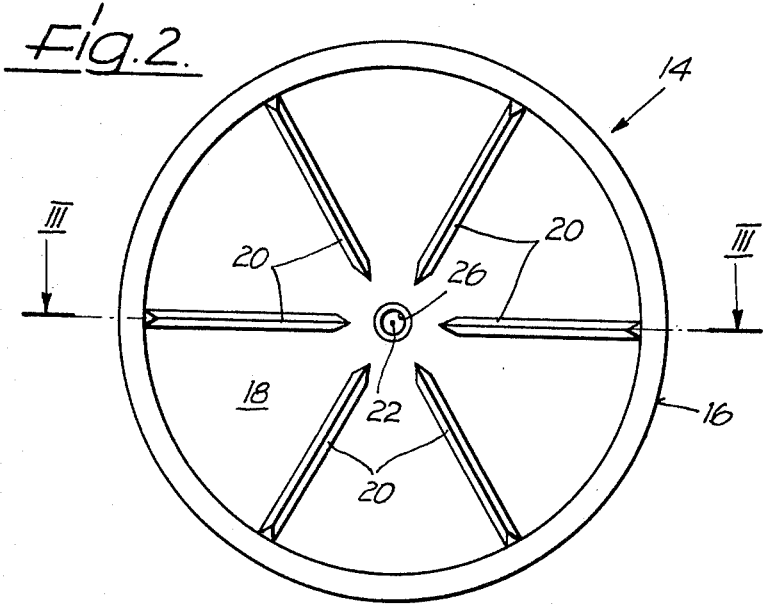
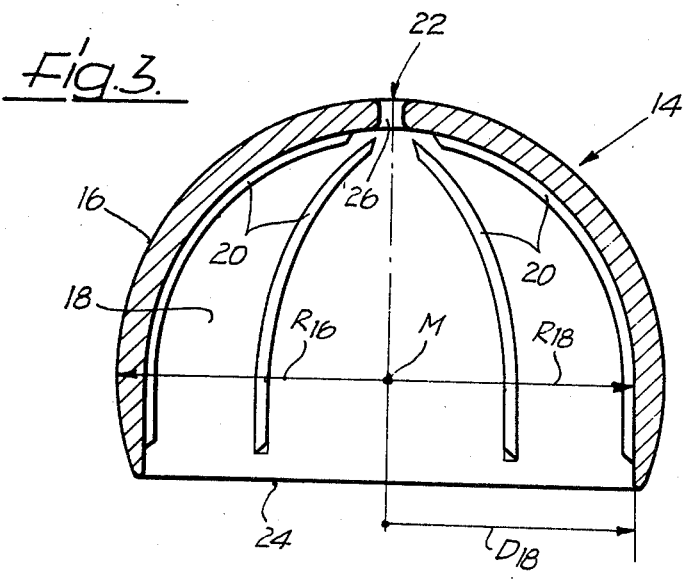

HIP CAPITULUM CAP FOR A HIP JOINT PROSTHESIS

BACKGROUND OF THE INVENTION

This invention relates to a hip capitulum cap for a hip joint prosthesis shaped essentially like half a hollow sphere.

Alloplastic hip joint end prostheses are presently used in two thoroughly different embodiments, of which there can be numerous variations and combinations. Familiar first of all are the so-called full prostheses, in which both the natural acetabulum, i.e., the hip socket in the pelvic bones, and the capitulum, or the head of the joint near the neck of the femur of the thigh bone, are replaced with an alloplastic prosthesis, i.e., a hip socket of metal or plastic which replaces the cartilage layer of the acetabulum and is fastened in the pelvic bones by means of bone cement, and a joint head of metal or plastic to which a shaft is integrally attached, the shaft being anchored in the femur medulla cavity by means of bone cement. Such conventional prostheses are disclosed, for example, in West Germman Publication DT-OS No. 1,912,630 and in West German Patent Specification DT-PS No. 1,566,386, FIGS. 1 and 2 thereof.

Since full prostheses are subject to a number of disadvantages, partial prostheses have also become available. In the case of known partial prostheses, only the capitulum, or the capitulum and the acetabulum, are dealt with and fitted with a pan- or bowl-shaped alloplastic, which replaces as necessary, either of the two damaged and artificially removed slide faces, for example, as shown in FIG. 3, of the aforementioned West German Patent Specification DT-PS No. 1,566,386. In this case, there is the possibility of attaching the alloplastic hip capitulum cap either in such a way that it floats loosely on the rounded remaining joint head, e.g., according to Smith-Peterson, or by force-locking it onto the remaining joint head by means of a press fit or form-locking it by means of an anchoring in the joint head and the neck of the femur, e.g., according to Luck. Heretofore, the anchoring was always achieved by means of a shaft adapted to the cap, e.g., in the form of a nail according to Judet or in the form of a screw according to Zanoli. None of the previously tested mountings of the hip head cap have proved entirely satisfactory. Obviously, loosening of the cap must be dealt with in the case of a floating mounting. Loosening of the cap can also occur as a consequence of the underwashing of the cap with synovial fluid, which loosening intensifies the already existing tendency for the formation of a bone tumor (callus) in the neck of the femur due to mechanical irritation by the edge of the cap.

With regard to a force-locked connection, the disadvantages of the floating mounting are only slightly alleviated and not entirely eliminated. If the cap loosens even once, the same conditions arise as in the case of a floating mounting. The disadvantages of a form-locked connection are somewhat similar to those of a full prosthesis, i.e., there is a possibility of damage to the bone tissue due to the polymerization heat emitted upon hardening of the bone cement (e.g. methyl methacrylate), a considerable amount of which must be used to ensure sufficient anchoring, and of unphysiological or abnormal conditions due to the application of load to the hip joint, which can lead to decomposition of the bone matter, loosening of the prosthesis and bone fractures. In the case of the absence of a hip socket cap, all three methods of fastening share the common disadvantage of gradual destruction of the cartilage layer in the acetabulum due to the relative movement between the acetabulum and the hip head cap.

SUMMARY AND OBJECTS OF THE INVENTION

In view of the foregoing situation, the invention proceeds from the general concept of providing a partial prosthesis with a hip socket cap formed of a self-lubricating plastic and a hip capitulum cap which is secured firmly and intimately to the capitulum with as little bone cement as possible.

It is therefore an object of the present invention to provide a cap of the sort described in the introduction and embodying the above-mentioned concept to insure a twist-resistant, close connection of head and cap.

The foregoing object as well as other objects, advantages and features are fulfilled by the invention by means of at least one surface unevenness or discontinuity on the inside of the hip capitulum cap and a perforation through the cap to the outside thereof.

The surface discontinuities guarantee security against rotation or twisting, while the perforation or opening allows the exit of displaced air and excess bone cement. In this way, it is possible to produce a relatively thin cement layer, which stabilizes the whole, between the treated capitulum and the inside of the cap. Such thin cement layer will produce very little polymerization heat, which heat will, in any case generally be absorbed by the metal cap and partially conducted further throughout the prosthesis. The same thin cement layer will also prevent penetration of synovial fluid into the slit between the capitulum and the cap.

In a peferred embodiment of the cap according to the invention, the inner surface unevennesses or discontinuities are formed on the inside of the cap by easily casted elevations, i.e., several ribs of essentially triangular cross-section, evenly distributed around the circumference and extending nearly from the vertex of the cap to its large edge. The preferred embodiment is furthermore distinguished by the fact that the opening or perforation is most advantageously located at the vertex and is in the form of a radial boring that is enlarged at its inlet and outlet ends, in order to allow excess bone cement to flow out with greater ease.

BRIEF DESCRIPTION OF THE DRAWINGS

In the following, the invention is explained in detail with reference to the preferred embodiment of the hip capitulum cap according to the invention as illustrated in the drawings, wherein:

FIG. 1 shows a central longitudinal cross-section of a hip joint with a prosthesis comprising an embodiment of the invention;

FIG. 2 is an enlarged view of the embodiment of the cap from the open end thereof; and FIG. 3 is a central cross-section along line III—III of FIG. 2, through the cap embodiment.

DETAILED DESCRIPTION OF THE PREFERRED EMBODIMENT

The hip joint prosthesis shown in FIG. 1 consists of a polyethylene hip socket bowl 6 anchored in force- and form-locked manner in the hip bone 4 by means of bone cement 2, and a cast alloy cap 14 attached to the joint capitulum 10 by means of a thin layer 8 of bone cement, which is form-locked onto the capitulum 10 of the thigh bone 12.

The cap 14, shown in detail in FIGS. 2 and 3, is essentially the shape of half a hollow sphere. The outer spherical slide face 16 of the cap 14 is about ⅓ more than half the surface of an imaginary sphere with the middle point M and radius $R_{16}$. The inner, uneven contact surface 18 of the cap 14 is composed essentially of the surface of an imaginary hemisphere with middle point M and radius $R_{18}$ smaller than $R_{16}$ and the surface of an imaginary disk-shaped circular cylinder having a diameter $D_{18}$ equal to $2R_{18}$. The unevenness of the inner surface 18 is produced by six ribs 20 of triangular cross-section, evenly distributed at 60° intervals around the inner spherical surface and which extend in the form of elevations from nearly the vertex 22 of the cap 14 to its lower large edge 24 and pass smoothly into the contact surface 18 at the upper end. Located at the vertex 22 is an opening essentially in the form of a "radial" boring 26, which is smoothly enlarged at its inlet and outlet ends, as can be seen in FIG. 3.

Although only a preferred embodiment is specifically illustrated and described herein, it will be appreciated that many modifications and variations of the present invention are possible in the light of the above teachings and within the purview of the appended claims without departing from the spirit and intended scope of the invention.

What is claimed is:

1. A hip capitulum cap for a hip joint prosthesis for cement fixation to a thigh bone comprising a cap member having inner and outer surfaces and shaped substantially in the form of half a hollow sphere, at least one surface discontinuity on the inner surface of said cap member and an opening through the wall of said cap member extending between the inner and outer surfaces thereof, wherein said cap member has a vertex, said opening being a radial boring located at said vertex and being enlarged at its outer end.

2. A hip capitulum cap according to claim 1, wherein said opening is enlarged at its inner end.

3. A hip capitulum cap for a hip joint prosthesis for cement fixation to a thigh bone comprising a cap member having inner and outer surfaces and shaped substantially in the form of half a hollow sphere, said cap member includes a vertex and a large edge, a plurality of elevations comprising triangular-shaped ribs evenly spaced about the inner surface of said cap member, said ribs extending from a point adjacent said vertex to a point adjacent said large edge, a radial boring located at the vertex which extends between the inner and outer surface of said cap member, said boring being enlarged at its inlet and outlet ends for receiving cement therein.

4. A hip capitulum cap according to claim 3 wherein said ribs pass smoothly into the inner surface near the vertex.

5. Method for securing a hip capitulum cap to a thigh bone capitulum without nails, screws or threads comprising the steps of:
   a. providing a capitulum cap having inner and outer surfaces and shaped substantially in the form of half of a hollow sphere, said cap member having a vertex and a large edge, elevations extending along said inner surface between said vertex and said large edge, an opening at the vertex passing through said cap member for readily receiving cement;
   b. preparing the capitulum of the thigh bone for receiving said capitulum cap;
   c. applying a thin layer of cement between said capitulum cap and said capitulum and permitting the surplus of said cement to penetrate said opening in said capitulum cap whereby said capitulum cap is fixedly secured to said capitulum.

* * * * *